United States Patent [19]

Weisman

[11] Patent Number: 5,747,019

[45] Date of Patent: May 5, 1998

[54] NAIL POLISH TOP COAT FREE OF TOLUENE

[75] Inventor: Martin J. Weisman, Canoga Park, Calif.

[73] Assignee: Charles S. Martens, Santa Margarita, Calif.

[21] Appl. No.: 832,124

[22] Filed: Apr. 3, 1997

Related U.S. Application Data

[63] Continuation of Ser. No. 528,677, Sep. 14, 1995, abandoned, which is a continuation-in-part of Ser. No. 347,943, Dec. 1, 1994, abandoned, which is a continuation of Ser. No. 148,891, Nov. 8, 1993, abandoned.

[51] Int. Cl.$^6$ .................................................. A61K 7/043
[52] U.S. Cl. .................. 424/61; 424/401; 424/78.37; 514/781
[58] Field of Search ................ 424/61, 401, 78-37; 514/781

[56] References Cited

U.S. PATENT DOCUMENTS

| | | | |
|---|---|---|---|
| 2,173,755 | 9/1939 | Fuller | 167/85 |
| 3,438,289 | 4/1969 | Michaelson et al. | 424/61 |
| 4,179,304 | 12/1979 | Rossomando | 424/61 |
| 4,409,203 | 10/1983 | Gordon et al. | 424/61 |
| 4,712,571 | 12/1987 | Remz et al. | 424/61 |
| 4,747,419 | 5/1988 | Flynn et al. | 132/73 |
| 4,749,564 | 6/1988 | Faryniarz et al. | 424/61 |
| 4,798,720 | 1/1989 | Holder | 424/61 |
| 5,093,108 | 3/1992 | Pappas et al. | 424/61 |
| 5,102,654 | 4/1992 | Castrogiovanni et al. | 424/61 |
| 5,130,125 | 7/1992 | Martin et al. | 424/61 |
| 5,206,011 | 4/1993 | Pappas et al. | 424/61 |
| 5,512,273 | 4/1996 | Martin | 424/61 |

FOREIGN PATENT DOCUMENTS 0 085 370  10/1983  European Pat. Off. .

OTHER PUBLICATIONS

"Information About Silicon Fluids", Dow Corning Corporation, dated 1988.
"Information About Volatile Silicone Fluids", Dow Corning Corporation, dated 1993.
"Cellolose Esters, Coatings Chemicals", Eastman Chemical Company, dated 1994.
"Eastman Cellulose Esters", Eastman Chemical Company, dated1988.
"Cellulose Acetate Butyrate for Coatings", Eastman Chemical Products, Inc. et al., dated 1986.
"Top Coats: The Crowning Glory", Nails, May, 1995, pp. 52–558.
Peirano, "Other Film Formers for Nail Enamels", American Perfumer and Cosmetics, vol. 84, No. 8, Aug. 1969 pp. 35–36.
Schlossman, "Nail Cosmetics", Cosmetics & Toiletries, vol. 101, Apr. 1986, pp. 23–27.
Schlossman, "Modern Nail Enamel Technology", J. Soc. Cosmet. Chem., 31, 29–36 (Jan./Feb. 1980).
Wimmel, et al., "The History of Nail Polish", Cosmetics & Toiletries, vol. 107, Sep. 1992, pp. 115–120.
Schlossman, "Trends in Nail Care Technology", Cosmetics & Toiletries, vol. 96, Apr. 1981, pp. 51–54.

*Primary Examiner*—Jyothsan Venkat
*Attorney, Agent, or Firm*—Fredrikson & Byron, PA

[57] ABSTRACT

A clear top coat composition for application over a wet nail polish, comprising cellulose acetate propionate ester, a mixture of solvents free of toluene, and a plasticizer, providing a dry non-tacky, non-brittle solid coat which is quick drying when applied over a nail polish while wet.

24 Claims, No Drawings

NAIL POLISH TOP COAT FREE OF TOLUENE

CROSS-REFERENCE TO RELATED APPLICATIONS

This application is a continuation of application Ser. No. 08/528,677, filed 14 Sep. 1995, now abandoned, which is a continuation-in-part of application Ser. No. 08/347,943, filed 01 Dec. 1994 now abandoned, which was a continuation of application Ser. No. 08/148,891, filed 08 Nov. 1993, and now abandoned.

BACKGROUND OF THE INVENTION

This invention relates to nail polishes and more specifically, to a composition for applying over a wet nail polish. Such a composition is sometimes clear but more often cloudy or slightly pigmented and is frequently referred to as a "top coat", which is applied over the color coat or coats.

There is very little teaching on this subject especially in relation to a composition that is applied over the wet nail polish and dries the nail polish in an exceedingly short period of time.

For many years the technology within the nail polish industry has remained constant. There has been little innovation outside of the ultraviolet light activated drying systems of today, one of which is disclosed in U.S. Pat. No. 5,118,495. Nail polishes have been applied as a single color coat starting at the turn of the century and in more recent times nail polishes have been applied in layers, with different layers having different compositions and being used for different purposes.

There are a few prior compositions patented for reducing the drying time of nail polish. One is Holder U.S. Pat. No. 4,798,720 which requires many steps to follow in the application and defeats any fast drying due to the application process. Another is a composition shown in Shansky U.S. Pat. No. 4,097,589. This composition utilizes a special copolyamide terpolymer to provide improved flexural strength.

However, none of these prior compositions provides the desired features of the ability to be applied over wet nail polish and the exceedingly short drying time.

There had never been a single application top coat for application over wet nail polish, without employing the use of nitrocellulose, in the history of the nail care industry until the advent of U.S. Pat. No. 5,130,125 to Martin et al. The composition of this patent solved the problem of an all-in-one product for drying fast while making the manicure more durable, maintaining a lasting high gloss and providing protection from harmful ultraviolet light rays which can alter the color of the underlying nail polish.

The problem that had always been present in the application of nail polish was the length of time required for the nail polish to dry, especially when each of a plurality of layers must set or start the drying process, before the next layer could safely be applied without dragging or streaking the underlying layer. Until recently the art of top coat technology was basically the same as pigmented nail polish, without the pigment, and employing a higher percentage of solvents to nitrocellulose thereby creating a drying effect at the surface. However, if any pressure is applied to the nail surface, sometimes hours after finishing the manicure, the surface can be smudged or scratched. The ultraviolet light boxes were the first at successfully drying nail polish in less than fifteen minutes (drying multiple layers). Then U.S. Pat. No. 5,130,125 singularly revolutionized the professional nail care industry. Before this patented invention the only place one could get nail polish to dry fast was at the professional salon. U.S. Pat. No. 5,130,125 was the first product that effectively dries nail polish typically in less than one minute if there is one layer of nail polish and one layer of top coated applied while the nail polish is still wet, without the use of any other tool or product. However, the top coat of this patent used toluene as a solvent.

Accordingly, it is an important objective of the present invention to provide a new nail polish top coat which can be applied over a wet layer of clear or colored polish and which will dry in a very short time, typically, in less than one minute, while being a clear composition and without the use of the solvent toluene.

U.S. Pat. No. 5,130,125 teaches the use of cellulose acetate butyrate (CAB), with the primary solvents being n-butyl acetate and toluene, and no nitrocellulose. This particular composition is ineffective as nail polish since it will not bond to the natural nail, and is used only as a top coat. In using CAB as a basis of the formulation to achieve an absolutely clear composition, toluene is employed; if toluene is exchanged for ethyl acetate the resulting composition is slightly cloudy although the end result is generally the same. To mitigate this "cloudy" problem one must slightly pigment the composition or sell the composition in a frosted bottle, both marketing nightmares. A top coat for nail polish should be clear so that there is no way it can alter the underlying nail polish.

The problem addressed and resolved by the present invention is how a clear composition can be obtained in a cellulose acetate solution without employing the use of toluene. It was discovered that the substance cellulose acetate propionate (CAP) has similar properties to CAB. The marketability of a clear solution as a top coat far exceeds the marketability of a cloudy product, a pigmented product, or a product sold in a frosted bottle. The present invention is a top coat only for use over wet nail polish which does not utilize toluene and which still remains absolutely crystal clear while drying the underlying nail polish in an exceedingly short period of time, and at the same time avoiding yellowing since there is no nitrocellulose present in the composition.

Nitrocellulose is the only organically derived component in many synthetically derived nail polish compositions, which, when it spoils or is exposed to light turns yellow/brown. The top coat of the present invention provides an excellent screen for the underlying nail polish by not allowing ultraviolet light emissions to alter the underlying nail polish.

The environmental issue of toluene in nail polish becomes a non-issue with the present invention, as there is not enough emitted into the air of even the poorest ventilated salon to cause any health hazard. With the substitution of ethyl acetate for toluene and substitution of CAP for CAB, the objects of the invention are achieved.

A prior composition for reducing the drying time is shown in the Holder U.S. Pat. No. 4,798,720. The composition is a mixture of commercially available products, a top coat polish, an acrylic nail powder, an acrylic nail primer, and an adhesive. The top coat polish is a commercial product with a nitrocellulose base. In use, the new composition is applied as a base coat layer, a color polish is coated on top of the first layer, another layer of the new composition is applied over the color polish as the third layer, another coat of color polish is applied over the third layer, and another coat of the new composition is applied over the second color polish as the fifth layer.

Another prior composition is shown in the Shansky U.S. Pat. No. 4,097,589. The composition of this patent utilizes a special copolyamide terpolymer to provide improved flexural strength.

However, none of these prior compositions provides the desired features of the ability to be applied over a wet nail polish and the exceedingly short drying time.

Accordingly, it is another object of the present invention to provide a new and improved clear top coat which does not utilize toluene nor nitrocellulose, and which can be applied over wet nail polish while drying in a very short time and at the same time avoiding yellowing.

SUMMARY OF THE INVENTION

A clear top coat composition for application over a wet nail polish, incorporating cellulose acetate propionate ester, a mixture of solvents for dissolving the cellulose acetate propionate ester, and a plasticizer, the cellulose acetate propionate ester and plasticizer being dissolved in the solvents, the plasticizer being present in an amount to provide a dry non-tacky, non-brittle solid coat and the cellulose acetate propionate ester being present in an amount which is effective to provide quick drying of the composition when applied over a wet nail polish, with improved hardness and gloss. However, the solvent toluene is neither needed nor desired, and its use is avoided. The same is true for nitrocellulose. A UV block and a smoother may be added when desired.

Other objects, advantages, features and results will more fully appear in the course of the following description.

DESCRIPTION OF THE PREFERRED EMBODIMENTS

The top coat composition is applied over a standard color nail polish while the polish is wet. The components of the composition are cellulose acetate propionate ester (CAP), solvents for CAP and a plasticizer. A ultraviolet bleaching material and a smoothing material may also be used. All embodiment of the composition are free of toluene.

The preferred constituents and sources for the constituents are set out in Table 1.

TABLE 1

| Material | Supplier |
| --- | --- |
| 1. ethyl acetate (solvent) | generic |
| 2. N-butyl acetate (solvent) | generic |
| 3. cellulose acetate propionate ester (general purpose) (CAP) | Eastman Chemical CAP 482-0.5 |
| 4. benzophenone-3 (UV block) | American Cyanamid |
| 5. dibutyl phthalate (plasticizer) | Ashland Chemical |
| 6. dimethylpolysiloxane (defoamer smoother) | BYK Chemical BYK 301 |

CAP (alcohol soluble) may also be used, available from Eastman Chemical as CAP 504-0.2.

The presently preferred embodiment of the top coat composition and the process of its manufacture are given in Example 1.

EXAMPLE 1

| | Quantity For One Gallon | % By Weight |
| --- | --- | --- |
| 1. ethyl acetate | 40 fl. oz. | 38.0 |
| 2. N-butyl acetate | 49 fl. oz. | 39.5 |
| 3. cellulose acetate propionate ester (general purpose) | 654 grams | 18.0 |
| 4. benzophenone-3 | 4 grams | 0.1 |
| 5. dibutyl phthalate | 4 fl. oz. | 4.0 |
| 6. dimethylpolysiloxane | 16 grams | 0.4 |

Charge solvents 1 and 2 into a high speed mixer. Add item 3 while running low speed. Run high speed 20 minutes until dissolved. Run low speed while adding items 4, 5 and 6. Run low speed at least one hour until clear solution is obtained. Fill in containers.

An alternative embodiment of the top coat composition and the process of its manufacture is given in Example 2.

EXAMPLE 2

| | Quantity For One Gallon | % By Weight |
| --- | --- | --- |
| 1. ethyl acetate | 32 fl. oz. | 30.0 |
| 2. ethyl alcohol | 8 fl. oz. | 8.0 |
| 3. isobutyl acetate | 37 fl. oz. | 30.0 |
| 4. methyl ethyl ketone | 12 fl. oz. | 9.5 |
| 5. cellulose acetate propionate ester (general purpose) | 510 grams | 1.40 |
| 6. cellulose acetate propionate ester (alcohol soluble) | 144 grams | 4.0 |
| 7. benzotriozole | 4 grams | 0.1 |
| 8. tricresyl phosphate | 4 fl. oz. | 4.0 |
| 9. dimethylpolysiloxane | 16 grams | 0.4 |

Items 1, 2, 3 and 4 are generic solvents. Items 5 and 6 are available from Eastman Chemical. Item 7 is a UV block available from American Cyanamid. Item 8 is a plasticizer available from FMC Corporation.

Charge solvents 1–4 into a high speed mixer. Add items 5 and 6 while running low speed. Run high speed 20 minutes until dissolved. Run low speed while adding items 7–9. Run low speed at least one hour until clear solution is obtained. Fill in containers.

These compositions provide a single clear protective coating for nail polish for application over wet polish, and dry quickly. The compositions do not yellow and prevent yellowing of the underlying layer. If desired a color can be, added to the top coat mixture. Soluble dyes such as D&C Violet #2, D&C Green #6, D&C Yellow #11 and D&C Red #17 can change the physical appearance of the liquid without affecting its clarity.

Alternative solvents may be used, including ketones, esters, glycol ethers, low levels of alcohols, aliphatic hydrocarbons and chlorinated solvents. Other plasticizers may be used, including dioctyl phthalate, diethyl phthalate, butyl benzyl phthalate, tricresyl phosphate. Other soluble absorbers may be used, including benzophenone, benzotriazole and triazine. Also, the CAP is an inherent ultraviolet inhibitor. If desired the UV block and the defoamer smoother constituents may be omitted.

The top coat composition may be applied directly over a wet layer of nail polish, and dries in a very short time, typically in less than one minute, hardening as it cures. The finished coat has high resistance to chipping, flaking, peeling and bubbling. The resulting finish has high gloss and gloss retention and remains "wet looking", especially when the smoother material is utilized. As the top coat composition cures, it bonds to the underlying nail enamel forming a protective shield for the color layer or layers. The embodiment incorporating the ultraviolet light blocking material inhibits the yellowing encountered with many nail polishes and permits longer wearing time.

I claim:

1. A clear top coat composition for application over a wet nail polish, comprising:

cellulose acetate propionate ester dissolved in a mixture of solvents free of toluene, and a plasticizer, said plasticizer being present in an amount to provide a dry non-tacky, non-brittle solid coat and said cellulose acetate propionate ester being present in an amount which is effective to provide quick drying of the composition when applied over a wet nail polish.

2. A composition as defined in claim 1 wherein said mixture of solvents consists of ethyl acetate and n-butyl acetate.

3. A composition as defined in claim 2 wherein said plasticizer is dibutyl phthalate.

4. A composition as defined in claim 1 wherein said mixture of solvents consists of ethyl acetate, ethyl alcohol, isobutyl acetate, and methyl ethyl ketone.

5. A composition as defined in claim 4 wherein said plasticizer is tricresyl phosphate.

6. A composition as defined in claim 1, further comprising an ultraviolet light blocking material.

7. A composition as defined in claim 6 wherein said ultraviolet light blocking material is benzophenone-3.

8. A composition as defined in claim 6 wherein said ultraviolet light blocking material is benzotriozole.

9. A composition as defined in claim 6, further comprising a smoothing material.

10. A composition as defined in claim 9 wherein said smoothing material is dimethylpolysiloxane.

11. A quick drying clear top coat composition for application over a nail polish while wet, consisting essentially, in percent by weight, of about:

ethyl acetate 38.0,

N-butyl acetate 39.5, cellulose acetate propionate ester (general purpose) 18.0, benzophenone-3 0.1, dibutyl phthalate 4.0, and dimethylpolysiloxane 0.4; and free of toluene.

12. A quick drying clear top coat composition for application over a nail polish while wet, consisting essentially, in percent by weight, of about:

ethyl acetate 30.0, ethyl alcohol 8.0, isobutyl acetate 30.0, methyl ethyl ketone 9.5, cellulose acetate propionate ester (general purpose) 14.0, cellulose acetate propionate ester (alcohol soluble) 4.0, benzotriozole 0.1, tricresyl phosphate 4.0, and dimethylpolysiloxane 0.4; and free of toluene.

13. A quick drying clear top coat composition for application over a wet nail polish, said composition having a solid material comprising about 18% by weight of said composition and a liquid content comprising about 82% by weight of said composition, said composition having a combination of cellulose acetate propionate ester as the solid material, and the plasticizer and solvents as the liquid contents, and free of toluene.

14. A composition as defined in claim 13 wherein said liquid content comprises an ultraviolet light blocking material as a component.

15. A composition as defined in claim 14 wherein said liquid content comprises a smoothing material as a component.

16. A composition as defined in claim 13 wherein said solvents comprise by weight about 38% ethyl acetate and about 39.5% N-butyl acetate without any toluene.

17. A composition as defined in claim 13 wherein said plasticizer comprises by weight about 4% dibutyl phthalate.

18. A composition as defined in claim 17 wherein said liquid content comprises by weight about 0.1% benzophenone-3 as an ultraviolet light blocking material.

19. A composition as defined in claim 18 wherein said liquid content comprises by weight about 0.4% dimethylpolysiloxane as a smoothing material.

20. A composition as defined in claim 13 wherein said solvents comprise by weight about 30% ethyl acetate, about 8% ethyl alcohol, about 30% isobutyl acetate, and about 9.5% methyl ethyl ketone.

21. A composition as defined in claim 13 wherein said plasticizer comprises by weight about 4% tricresyl phosphate.

22. A composition as defined in claim 21 wherein said liquid content comprises by weight about 0.1% benzotriozole as an ultraviolet light blocking material.

23. A composition as defined in claim 22 wherein said liquid content comprises by weight about 0.4% dimethylpolysiloxane as a smoothing material.

24. A clear top coat composition for application over a wet nail polish, comprising:

cellulose acetate propionate ester dissolved in a mixture of solvents free of toluene, and a plasticizer, said plasticizer being present in an amount to provide a dry non-tacky, non-brittle solid coat and said cellulose acetate propionate ester being present in an amount which is effective to provide quick drying of the composition when applied over a wet nail polish, with said cellulose acetate propionate ester being present in percent by weight of about 18, said solvents being present in percent by weight of about 18.0, and said plasticizer being present in percent by weight of about 4.

* * * * *